United States Patent
Fornarelli

(10) Patent No.: US 10,111,468 B2
(45) Date of Patent: Oct. 30, 2018

(54) VAPORIZATION DEVICE

(71) Applicant: DB INNOVATION INC., Chicago, IL (US)

(72) Inventor: Thomas Fornarelli, Chicago, IL (US)

(73) Assignee: DB INNOVATION INC., Chicago, IL (US)

( * ) Notice: Subject to any disclaimer, the term of this patent is extended or adjusted under 35 U.S.C. 154(b) by 0 days.

(21) Appl. No.: 15/181,323

(22) Filed: Jun. 13, 2016

(65) Prior Publication Data
US 2017/0354180 A1    Dec. 14, 2017

(51) Int. Cl.
| | |
|---|---|
| *A24F 47/00* | (2006.01) |
| *H05B 1/02* | (2006.01) |
| *A61M 11/04* | (2006.01) |
| *A61M 15/06* | (2006.01) |
| *A61M 15/00* | (2006.01) |
| *G08C 17/02* | (2006.01) |

(52) U.S. Cl.
CPC ......... *A24F 47/008* (2013.01); *A61M 11/042* (2014.02); *A61M 15/06* (2013.01); *H05B 1/0244* (2013.01); *A61M 15/0003* (2014.02); *A61M 15/0021* (2014.02); *A61M 2205/276* (2013.01); *A61M 2205/3368* (2013.01); *A61M 2205/587* (2013.01); *A61M 2206/16* (2013.01); *G08C 17/02* (2013.01)

(58) Field of Classification Search
CPC ...... A24F 15/18; A24F 47/008; H02J 7/0044; H02J 7/0047
USPC .................................. 320/328, 329
See application file for complete search history.

(56) References Cited

U.S. PATENT DOCUMENTS

| | | |
|---|---|---|
| 6,234,167 B1 | 5/2001 | Cox et al. |
| 6,345,739 B1 | 2/2002 | Mekata |
| 9,271,528 B2 | 3/2016 | Liu |
| 9,301,547 B2 | 4/2016 | Liu |
| 9,549,573 B2 * | 1/2017 | Monsees ................ H05B 3/04 |
| 2007/0068523 A1 | 3/2007 | Fishman |

(Continued)

FOREIGN PATENT DOCUMENTS

WO      2016005602 A1    1/2016

OTHER PUBLICATIONS

'The Hell's Gate V2 By Yep—Review' (SoulOhm) Mar. 30, 2016 [online] retrieved from <URL: https://www.youtube.com/watch?v=4cn7kPxXFCk> entire document, especially video demonstration 2:17-2:50, 4:49-4:58, 6:15-6:42, 7:06-7:35; video snapshot 1:49, 3:58, 8:13.

(Continued)

*Primary Examiner* — Hien Vu
(74) *Attorney, Agent, or Firm* — Flener IP & Business Law; Zareefa B. Flener

(57) ABSTRACT

A vaporization device is provided having a plurality of pens each having a battery, a mouthpiece, and a ventilated end. A vaporization device is also provided which is disposable having a plurality of pens, each having a vaporization chamber containing a coil, a battery, a PCB, a sensor, and a tank containing e-liquid for vaporization in the pen vaporization chamber through the coil of the pen to create a vaporization product which is mixed in a vapor port of the device through which a plurality of vaporization products are delivered to a user through the mouthpiece of the device in a single vaporization event.

12 Claims, 11 Drawing Sheets

(56) References Cited

U.S. PATENT DOCUMENTS

| | | |
|---|---|---|
| 2013/0276804 A1 | 10/2013 | Hon |
| 2013/0340775 A1 | 12/2013 | Juster et al. |
| 2014/0060556 A1 | 3/2014 | Liu |
| 2014/0123989 A1 | 5/2014 | LaMothe |
| 2014/0190503 A1 | 7/2014 | Li et al. |
| 2014/0261488 A1* | 9/2014 | Tucker .................. A24F 47/008 131/328 |
| 2014/0283825 A1 | 9/2014 | Buchberger |
| 2015/0020826 A1 | 1/2015 | Liu |
| 2015/0090253 A1 | 4/2015 | Farrow |
| 2015/0136158 A1* | 5/2015 | Stevens ................. A24F 47/008 131/329 |
| 2015/0164145 A1 | 6/2015 | Zhou |
| 2016/0106936 A1* | 4/2016 | Kimmel ................ A24F 47/008 128/202.21 |
| 2016/0150828 A1* | 6/2016 | Goldstein ............. A24F 47/008 392/387 |
| 2016/0353800 A1 | 12/2016 | Di Carlo |

OTHER PUBLICATIONS

'VapePorn—Chain Smoker Dual Mech Mod explained' (TheSmokenjoey) Apr. 24, 2015 [online] retrieved from <URL: https://www.youtube.com/watch?v=4cn7kPxXFCk> entire document; video snapshot.

International Search Report for PCT/US2017/037206, dated Sep. 1, 2017.

Written Opinion of Intl. Search Authority, PCT/US2017/037206, dated Sep. 1, 2017.

\* cited by examiner

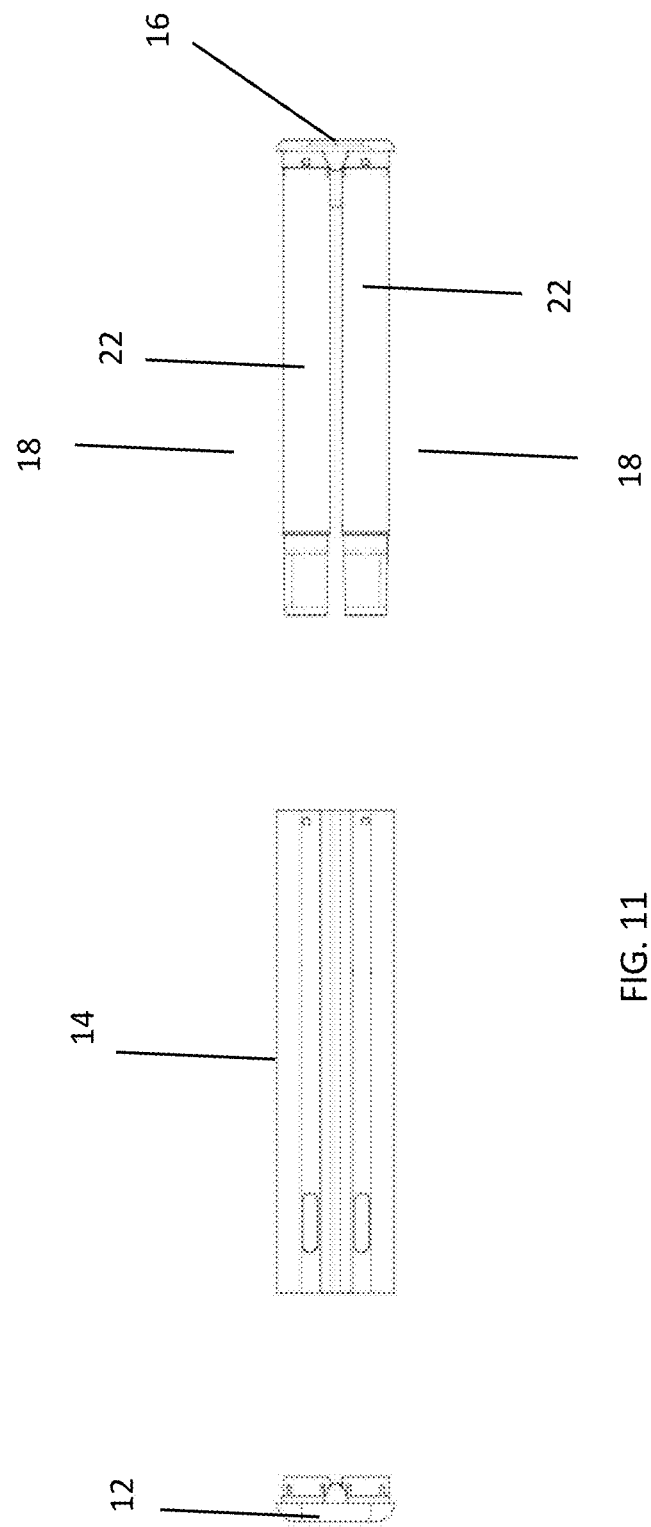

VAPORIZATION DEVICE

FIELD OF THE INVENTION

The present invention relates to a vaporization device. More specifically, the present invention relates to a vaporization device having a plurality of tanks.

BACKGROUND

Vaporization devices include various common components including a coil, a vaporization chamber, a battery, a mouthpiece, and a reservoir. The reservoir is filled with electronic liquid ("e-liquid") which can be composed of essential oils and other chemicals such as nicotine and/or cannabinoids. A wick acts as a bridge between the e-liquid in the reservoir and the vaporization chamber. It is the coil that plays a key element in vaping at the right temperature for the particular e-liquid as it is responsible for reaching a certain temperature maintaining the same. Not enough heat means no vapor, too much heat and the device will not serve its purpose, and could potentially produce toxins.

A vaporizer pen works by heating up the e-liquid, to a specific temperature then releasing its active substance/essential oils in the form of water vapor. By using this particular process, the plant materials are not burned, and this means that there is no combustion (emission of smoke or other toxic chemicals like carbon dioxide), unlike that of traditional smoking of tobacco and other dry herbs.

As a vape pen is portable, it must be properly charged in order to work. A lithium-ion battery is mostly used with cordless vaporizers, and these batteries can either be charged using a wall adapter, portable charging case, or a USB charger. Once the lithium-ion battery is fully charged, a device is ready to use. Using a vaporizer pen involves inhaling directly through the tip of a mouthpiece on the device. When sensors inside the cylinder or tube sense the inhalation via a change in pressure or otherwise, they activate what is known as the atomizer to heat up. When the atomizer heats up—it begins to heat the e-liquid in the reservoir. The substance vaped is heated to a specific temperature (below that of combustion/smoke), but still creates the tasty water vapor from the essential oils of the material.

The e-liquid that is often used with a vapor pen comes in a variety of strengths of nicotine, ranging from 0 to 36 mg, with a normal cigarette having approximately 12 mg by comparison. Often vaporization pens are utilized to cut down on nicotine use, by moving from higher levels of nicotine to lower levels of nicotine, to eventually zero nicotine, while at the same time, achieving an enjoyable vaping experience by vaping hundreds of the available e-liquid flavors on the market.

Vaporizers work by using heating elements that heat up the herbs to the point of boiling or vaporization, but not too hot to otherwise burn the botanicals. Many portable vaporizers feature efficient heating systems with adjustable temperature settings to give greater freedom to get to the exact temperature preferred.

When vaping marijuana, for example, vaping temperatures ranging from 175° C. to 190° C. tend to result in more sedative or relaxing effects, also depending in part on the strain of the plant involved. But, any temperature that goes beyond 230° C. renders the herbs to combustion. Many vaporization pens do not feature adjustable heat settings, and therefore, it is often more difficult to get the best result from a mix of different chemicals, and even from a single herb or essential oil due to the burning of some quickly at a particular temperature and dominating the flavor/effect. Each herb or plant can have hundreds of cannabinoids, each of which may have a unique boiling and vaporization temperature.

Tetrahydrocannabinol (THC) is more often vaped at a temperature of between about 155° C. to 160° C. It is perhaps the most essential and sought-after cannabinoid among medical and most especially recreational marijuana users. Taken in adequate doses, THC can help alleviate symptoms of pain and other physical discomfort. Some studies have also shown that this cannabinoid protects brain cells and can even promote growth. Different cannabis strains contain varying levels of THC and proportions of other cannabinoids. For example, the Sativa varieties boast the highest amount of THC, while Indica ones contain more of the other health-giving cannabinoids than the more psychoactive THC.

Cannabidiol, otherwise known as CBD, has a vaping temperature of between about 160° C. to 180° C. This cannabinoid is as abundant as THC in any cannabis plant. And while the major controversies surrounding marijuana use actually focus on the effects of THC with all those reported highs and psychomotor impairments in large doses, CBD offers a more promising use of cannabis in the medical field.

Contrary to common perception, CBD is non-psychoactive, meaning that it does not interfere with your judgment or motor skills. Rather, and more importantly, are the therapeutic effects of CBD. These include the cannabinoid's anti-convulsant (suppresses epileptic seizures), anti-cancer (hampers the growth of tumor cells), anti-inflammatory and anti-oxidant properties (fights against neurodegenerative disorders such as Alzheimer's disease). Studies also show that CBD alleviates anxiety and depression.

Unlike THC, Cannabidol ("CBN"), with a vaping temperature of about 185° C. has the opposite effect of inducing sleep, making this a good drug for those suffering from insomnia. But beyond its sedative effects, CBN has also been found to combat methicillin-resistant *Staphylococcus aureus* (MRSA), a powerful bacteria that's been hard to eliminate because of its resistance to antibiotics. Cannabinol does not occur naturally in fresh cannabis. Instead, it becomes the byproduct formed as THC degrades over time.

Tobacco vaporizes at between about 120-150° C. (257-302° F.).

Of course, cannabis herb is not the only plant vaporized. Other herbs are also popular for vaping and offer soothing and relaxing sensations when vaporized and inhaled. In fact, many of these plants contain substances that have more subtle psychoactive effects.

For example, some preferred vaping temperatures for the following dry herbs are: eucalyptus, 266° F. (130° C.); hops, 309° F. (154° C.); chamomile, 374° F. (190° C.); lavender, 266° F. (130° C.); lemon balm, 288° F. (142° C.); sage, 374° F. (190° C.); thyme, 374° F. (190° C.). These temperatures provide aromatherapy benefits as well. These temperatures are also ideal for aromatherapy.

The composition of essential oils is typically complicated. Essential oils are constituted by terpenoid hydrocarbons, oxygenated terpenes and sesquiterpenes. They originate from the plant secondary metabolism and are responsible for their characteristic aroma. Although the essential oils have a great number of components, the ones of commercial interest are generally those composed of one or two major components, which provides them with accurate features. Nonetheless, in some cases, the minor components are also important because they might provide the oils with exquisite perfume, that is why this kind of material must be handled with care. The extraction, preservation and conditioning of such a material are very important in order not to alter its composition, and equally, when vaporized, effective temperatures should be maintained to get the most benefit from the same. Each essential oil has a different boiling point and contains a variety of different terpenes (which are the fragrance molecules)—and it is possible to experience a different flavor and effect from one temperature to the next.

This balance of and reaction between constituents is also what makes one oil more or less toxic than another. The proportion of a toxic constituent in one oil may be balanced by other constituents which make the potential toxin less significant and allow the oil to be useful in therapy.

E-liquid contains at least four ingredients including propylene glycol ("PG") and vegetable glycol ("VG"), nicotine and/or cannabis, and water. Propylene glycol is relatively thin in consistency, is runnier than the VG variety, and is more easily absorbed by the wick. The low density also lends itself to less build up on the heating element of the pen as fast as when thicker vegetable glycerin liquid is used. VG is a considerably thicker solution, compared to PG. On its own, VG has a slight sweet taste which also makes the e-liquid sweeter and the flavors a little difficult to detect. Although mixing e-liquid to create a personalized blend is becoming more common, it is not the easiest of tasks due to the different consistencies of PG, VG and water.

PG boils at 188° C. (370° F.) while VG boils at 290° C. (554° F.). Thus, vaping at 100% VG involves higher coil temperatures (water does not mitigate temps since it evaporates early).

As mentioned, vaporizing pens are not provided with heat control mechanisms. With pens, a closed circuit, administered by a sensor, for instance, but not limited to, an air sensor or pressure sensor, in communication with the printed circuit board (PCB) and the battery, activates the heating element which then vaporizes the exposed herbs or nicotine in the e-liquid which are delivered to the vaporization chamber. There is no way to easily adjust the temperature in vaporizing pens. Some attempts to control a vaping temperature of a single e-liquid in a pen, which can contain many different chemicals with desired effects, have been proposed including pressing and holding an activation button (if it has one) down to heat the coil, releasing the button a few seconds after. Then pressing again and releasing again in a rhythmic sequence, thereby preventing the coil from operating at full capacity, and resulting in a slightly cooler temperature and even battery savings. Another proposal is for when not inhaling for a long time, turning the vaporizer off, rather than relying on the automatic shut-off mechanism of the device to save on battery and vapors. Other vaporizers are designed with an embedded heating element so that the herbs inside the chamber are not directly exposed, thus keeping the materials from burning.

Overheating a coil will burn the chemicals in an e-liquid such that at least the beneficial effects are not obtained, and at the most, the burned chemicals or even the wick can be toxic, harmful and have an unpleasant taste. It is difficult to mix different e-liquids for vaporization at least because different e-liquids have different viscosities and do not always easily mix; and e-liquids contain different herbs with different chemicals which, as mentioned above, have different temperatures of vaporization.

A device is needed, therefore, which can more completely vaporize a plurality of chemicals in a plurality of e-liquids at the same time, thereby providing a vaping experience which combines the effects of each component in a particular e-liquid at the same time.

SUMMARY OF THE INVENTION

The present invention is related to a device with a plurality of pens, each able to accommodate a tank holding a unique e-liquid for vaporization.

The present invention also relates to a device with a plurality of reservoirs each comprising an e-liquid that cannot easily be mixed with the other for vaporization in a single vaporization at a single coil temperature for a combined vaporization product for inhalation by a user.

The present invention further relates to a device which is disposable.

The present invention even further relates to a device which is rechargeable, and also accommodates removably affixed tanks which can be exchanged as desired with other tanks containing a different e-liquid and components.

The present invention moreover relates to a device which can mix a plurality of e-liquids in a vaporization chamber and vaporize the mixture at one temperature.

The present invention relates to a device which can vaporize an e-liquid and combine the vaporization produce with e-liquid vaporized by a different coil at a different temperature and in a different vaporization chamber, while combining or mixing the plurality of vaporization products produced from each vaporization together in a vapor port for inhalation by the user.

BRIEF DESCRIPTION OF THE DRAWINGS

FIG. 11 illustrates an exploded view of an embodiment of the device in accordance with the principles of the present invention.

DETAILED DESCRIPTION OF THE DRAWINGS

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Further, it should be understood that, although steps of various claimed methods may be shown and described as being in a sequence or temporal order, the steps of any such method are not limited to being carried out in any particular sequence or order, absent an indication otherwise. That is, the claimed method steps are considered capable of being carried out in any sequential combination or permutation order while still falling within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Figure 1:
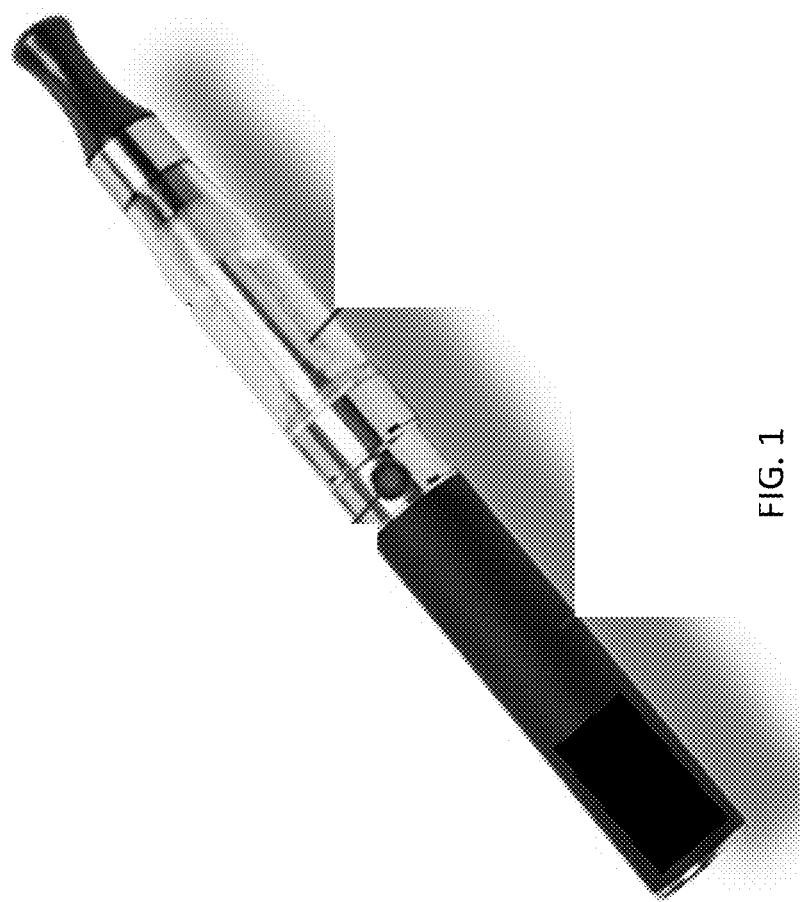
FIG. 1 illustrates a prior art electronic pen or cigarette.

FIG. 1 illustrates an electronic cigarette ("e-cigarette") or electronic pen which is commonly understood and known in the art. Depicted is a front end where the mouthpiece is, adjacent and operatively connected to the tank which contains e-liquid. The tank has a reservoir for e-liquid which is delivered to the coil, which when heated vaporizes the e-liquid. The vaporization process is supported by a sensor recognizing a change in pressure, communicating the same to some sort of printed circuit board or microprocessor which can connect the battery to heat the coil. As is illustrated, e-pens or e-cigarettes deliver vaporized e-liquid to a user through the mouthpiece. The vaporized e-liquid travels through a vapor port up to the mouthpiece and into the user's mouth and lungs.

Figure 2:
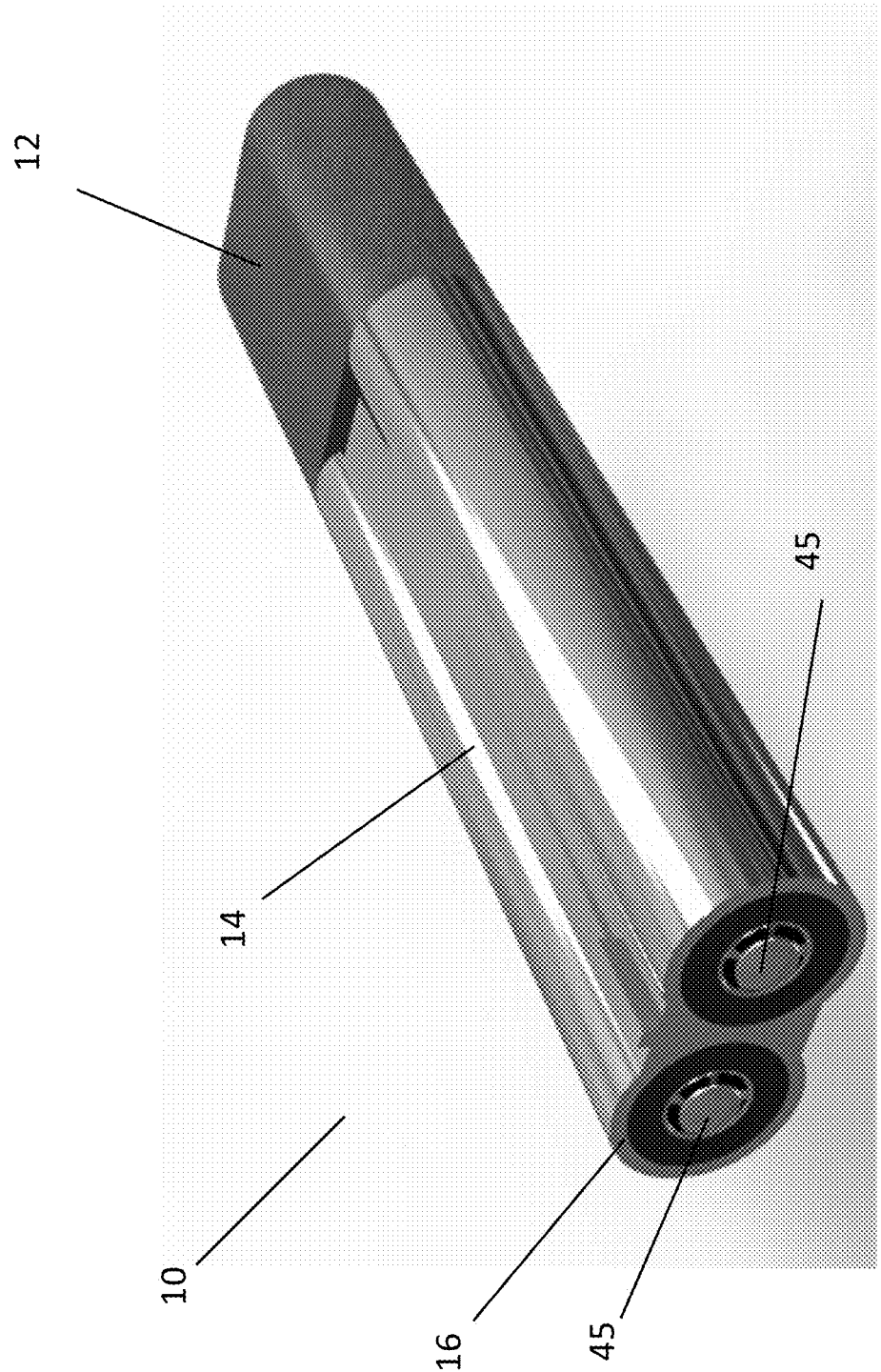
FIG. 2 illustrates an embodiment of the device in accordance with the principles of the present invention.

FIG. 2 illustrates a perspective view of the vaporization device 10 with a first end having a mouthpiece 12 adjacent to a body 14 at a first end of the body, and at a second end of the body 14, the body 14 is adjacent to a ventilated end 16 on a second end of the vaporization device 10 opposing the first end. The ventilated end 16 is provided with a plurality of airflow apertures 45 which can direct air flow through the vaporization device 10. Inside the body 14 of the device 10 is, unlike the pen or e-cigarette shown in FIG. 1, is housed a plurality of pens 18 which each have a battery and either threading compatible with retaining a tank 24 which has a vaporization chamber 26 and a coil 34 therein, or each pen can have a battery 22 plus a vaporization chamber 26 and a coil 34 wherein the vaporization chamber 26 can threadingly receive a tank 24 which has a reservoir containing e-liquid for vaporization (see e.g. FIG. 5). Once the tanks 24 having a vaporization chamber plus coil are appended to the pen battery 22, or tanks 24 appended to a battery 22 having also on the battery a vaporization chamber 26 plus coil 34, the vaporization product produced from a vaporization event travels along a vapor port (not shown) through an aperture 42 (see e.g. FIG. 3) in the mouthpiece 12 to be drawn into a user's mouth and/or lungs. The aperture 42 can be any size that is effective for drawing vapor into the mouth of a user, and the mouthpiece 12 can be any shape and size that is ergonomically suitable for accommodating a plurality of pens 18 and a vapor port through which vaporization products are delivered from the plurality of vaporization chambers 26 in the mouthpiece to the aperture 42.

Figure 3:
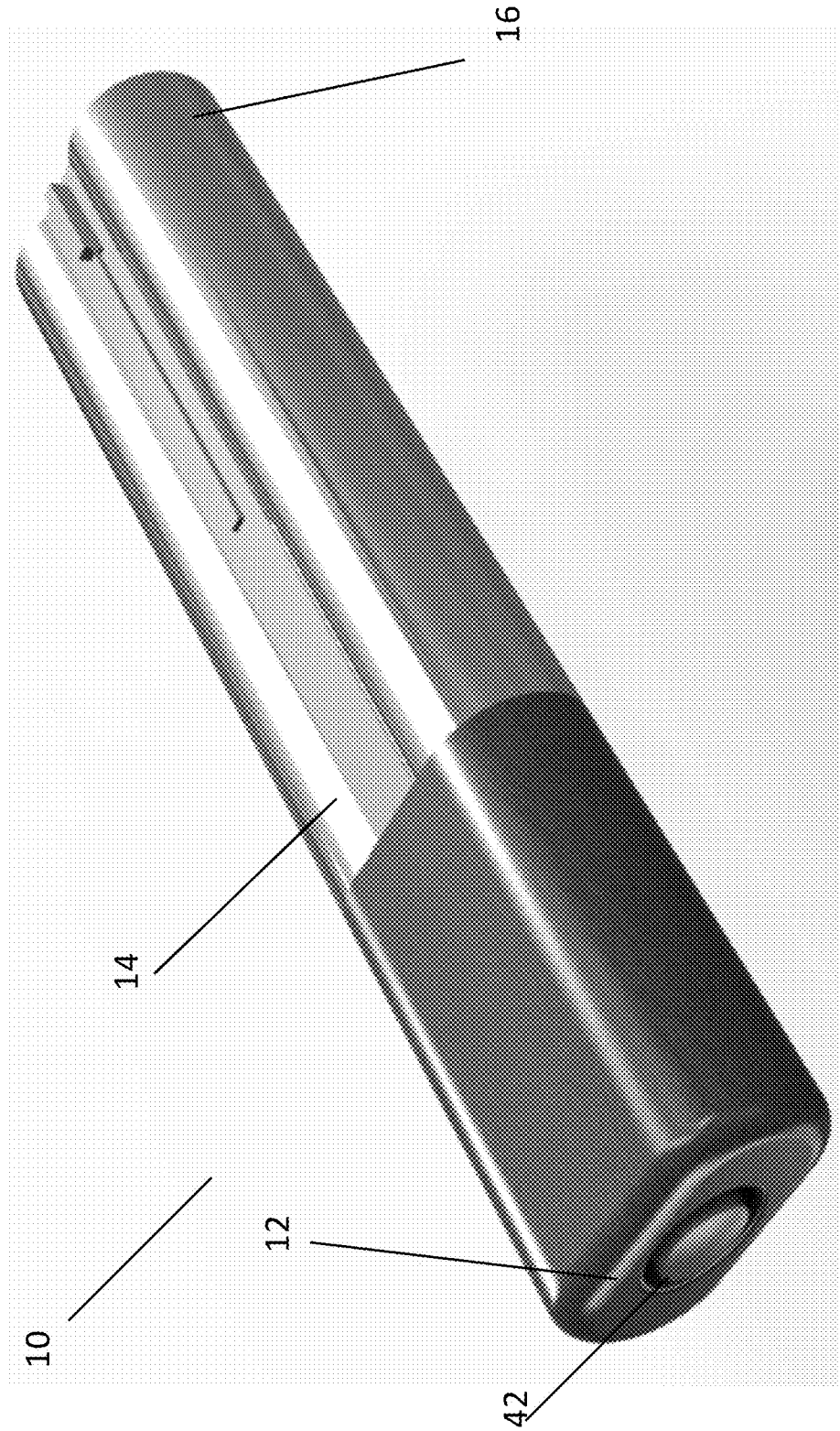
FIG. 3 illustrates an embodiment of the device in accordance with the principles of the present invention.

Preferably, the number of airflow apertures 45 is the same as the number of pens 18 (see e.g. FIGS. 2 and 3 illustrating two pens and two airflow apertures 42) housed in the body 14. This allows for air to flow to each pen through the inside of the device, and also in an embodiment wherein each pen 18 is also provided with its own sensor 20, to direct air flow to each sensor 20 on each pen 18.

FIG. 3 provides another perspective view of the device 10 showing the mouthpiece 12, the body 14, and the ventilated end 16.

Figure 4:
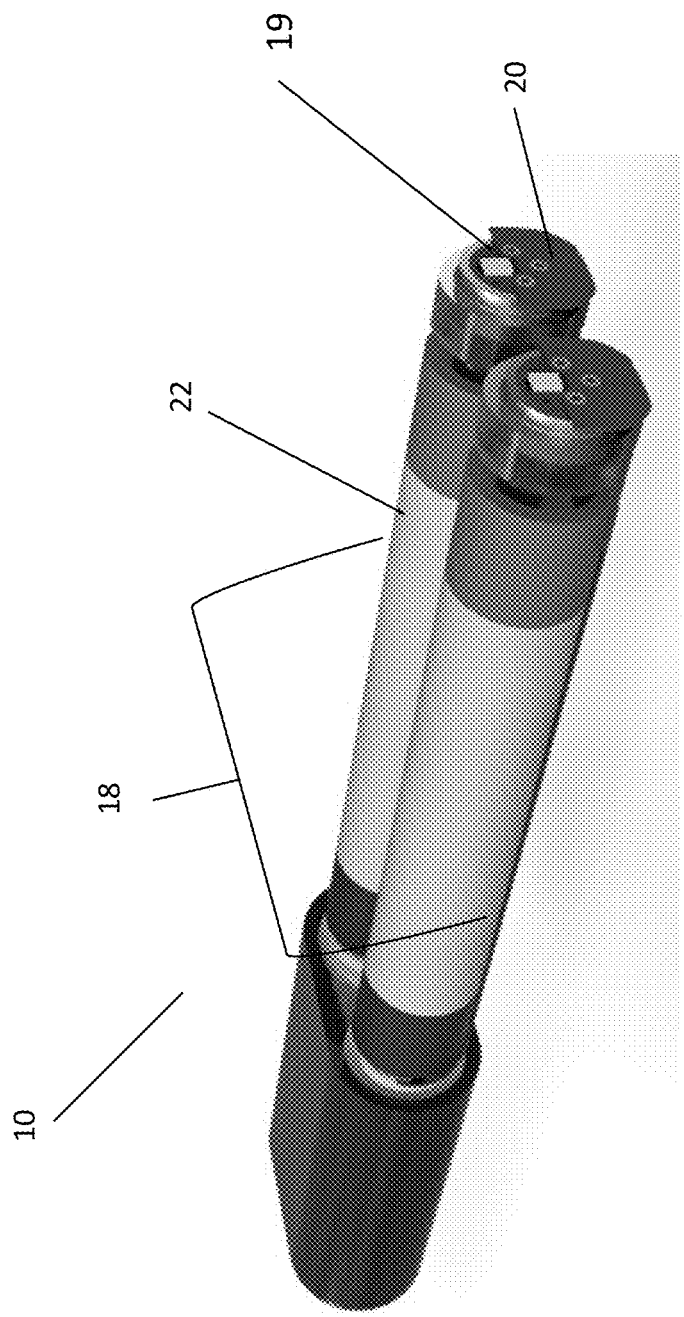
FIG. 4 illustrates an embodiment of the internal components of the body and the ventilated end of the device in accordance with the principles of the present invention.

FIG. 4 illustrates some of the internal components of the vaporization device 10. In this embodiment is shown that the vaporization device 10 is provided with a plurality of pens 18, and in this particular embodiment there are two pens 18. Each pen 18 has its own printed circuit board ("PCB") 19, a sensor 20 for instance, but not limited to, a pressure sensor or an air-flow sensor 20, and a battery 22, which together control the vaporization of e-liquid components in the tank of the pens 18. The PCB may include, for example, but is not limited to, a processing unit, a memory unit, a plurality of timers, and other suitable electrical components. Electronic components of the pen 18 are fixed to the PCB, which mechanically supports and electrically connects components of the assembly using tracks, pads, and other features etched from conductive sheets laminated onto a non-conductive substrate. In some embodiments, the electronics of the PCB is composed of a synthetic material that is thin and flexible. A thin and flexible PCB allows the same to conform to the shape of the electronic cigarette. A PCB is composed of materials such as, but not limited to, polyimide, polyethylene naphthalate, poletherimide, fluoropolymers, transparent conductive polyester, and other suitable materials for flexible electronics.

Figure 5:
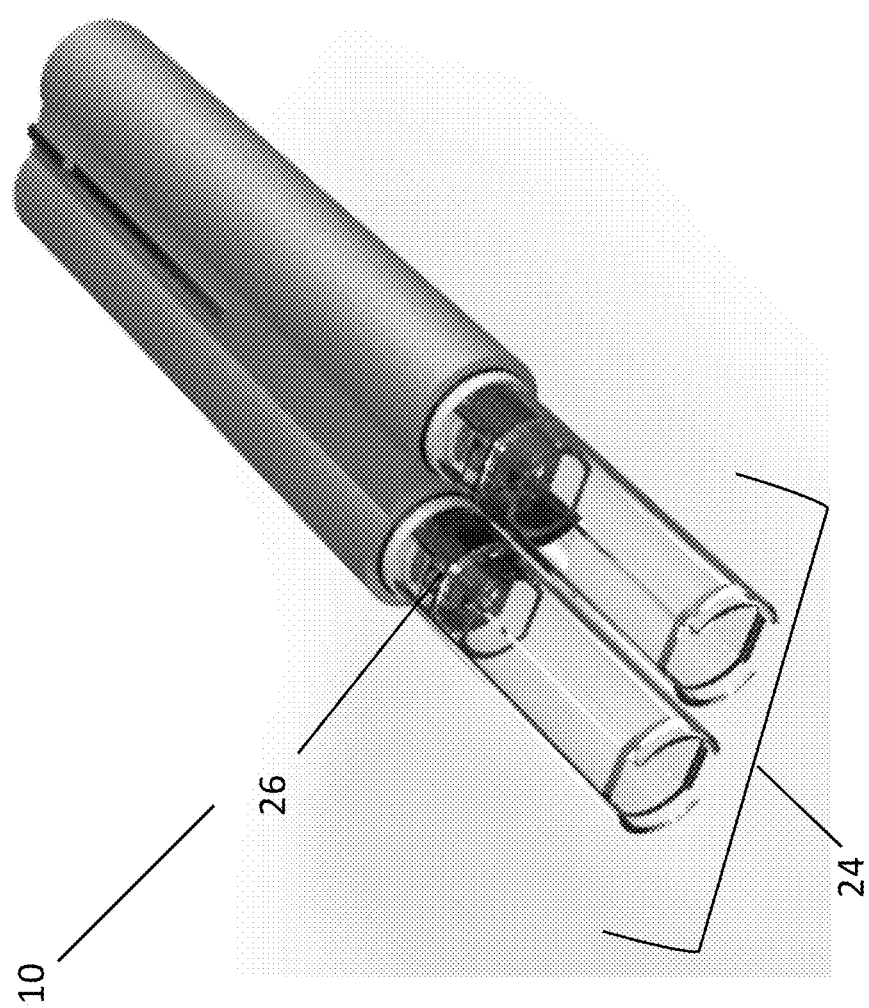
FIG. 5 illustrates an embodiment of the device in accordance with the principles of the present invention.

FIG. 5 illustrates the mouthpiece end of the vaporization device 10. In this particular embodiment, illustrated are two tanks 24 in which e-liquid is received in the reservoirs 28 (see e.g. FIG. 9) of each of the tanks 24. In this embodiment, each tank 24 is attached to a vaporization chamber 26 of each single pen 18. In this way, for each pen 18, a chamber 26 may vaporize a different e-liquid composition, be it an essential oil and/or nicotine and/or different strains of cannabis and/or different consistencies and percentages of PG, VG, and water, and can vaporize at a unique temperature apart from another pen of the plurality. This is accomplished by each pen 18 of the plurality of pens being provided with a PCB, battery 22, and sensor 20 to specifically control the temperature and timing of vaporization of the e-liquid in the tank 24 of each pen 18 so as to most closely achieve an ideal vaporization temperature for the molecules in the e-liquid. The vaporization product from each of the vaporization chambers 26 can be mixed in a vapor port for inhalation through the aperture 42 in the mouthpiece 12 of the device 10.

The battery 22 of the device 10 can be rechargeable, can be recharged/charged via induction charging, and/or can be charged by a wall electrical outlet, and/or by accommodating a USB to a computer to recharge/charge. In some embodiments, the battery 22 is a lithium battery, a lithium-ion battery, a nickel-cadmium ("NiCd") battery, a nickel-metal hydride ("NiMH") battery, or another suitable battery type. The battery 22 of each of the pens 18 will be of suitable shape and length to essentially provide the look and feel of an electronic cigarette. In the case of a rechargeable embodiment of the device 10, it is possible for a rechargeable device 10 to be provided with LED lights such that a pattern for charging is detected on the body 14 or the end 16. For example, but not limited to, a pattern whereby lights flash in a pattern when the vaporization device 10 is being charged, and a different pattern when finished.

When the battery is operationally afixed to the tank 24, and the user inhales, each of the pen sensors 20 communicates with the PCB and battery in order that the e-liquid in each of the tanks 24 is vaporized in the chamber 26 producing a vaporization product specific to the e-liquid which has been vaporized at the specific temperature dictated by the PCB of the particular pen 18. Thereafter, the vaporization product from each of the plurality of pens 18 and thus e-liquids is mixed in the vapor port and inhaled through a single mouthpiece 12. In this way, the pleasure of a plurality of different e-liquid vaporization products can be attained in a single vaporization event and at a more effective temperature for each of the plurality of electronic cigarettes 18. This prevents over-heating, creating toxins and bad tastes, and allows for the most accurate and beneficial vaporization of targeted chemicals in each e-liquid, and the e-liquid itself considering PG, VG, and mixes thereof, require different vaporization temperatures. In fact, by providing different vaporization temperatures across each of a plurality of pens 18, a VG heavy e-liquid needing to be vaporized at a higher temperature can be filled in a tank 24 which does not have a cotton wick, and paired with a tank carrying an e-liquid requiring a lower temperature and using a cotton wick, which is not recommended for vaporizing e-liquid which has high VG content. In this way, VG based e-liquid can be vaporized at a high temperature, without evaporating water while burning a cotton wick creating toxins, while at the same time vaporizing a different e-liquid requiring a lower temperature for producing a beneficial vaporization product.

In a disposable embodiment of the device 10, upon the final vaporization of the e-liquid in the reservoir the mouthpiece 12 can be immovably affixed to the body 14. In such an embodiment, the battery 22 need not be rechargeable, and the device in an embodiment may be provided with a window to visualize the e-liquid to know whether the e-liquid is finished.

In another embodiment, the device 10 is reusable, rechargeable, and the tanks replaceable. In such an embodiment, the mouthpiece 12 of the vaporization device 10 is removable, whereby the mouthpiece 12 is entirely removable, or preferably, moveably retained on the body 14 by for instance, but not limited to, a hinge, or a hook and loop, or a tie, whereby the mouthpiece 12 can be removed so as to reveal the replaceable tanks 24. When entirely removed, the mouthpiece 12 can be removably affixed to the body, for instance, but not limited to, a snap fit via a hook and groove accommodation. The mouthpiece 12 can also be configured to act as a circuit breaker such that when the mouthpiece 12 is not secured to the body 14, the battery circuit for vaporization is open and inoperable thus providing a safety feature for the device 10, for example for travel or when not in use. When the tanks 24 are operationally secured to the battery 22 and the pen 18, the mouthpiece 12 can be closed thus allowing the device 10 to be activated through a detected pressure change effecting the sensor and the PCB thus controlling vaporization.

In a reusable embodiment, the tanks 24 can be exchangeable/replaceable whereby a tank 24 can be disconnected from the pen 18 and another affixed thereto as desired. In this way, the user can have the pleasure of combining different vaporization products produced by different e-liquids in different tanks 24. In some embodiments, the disposable tank 24 is provided with a leak proof cap, which can be removably affixed thereto in order that after removal from the pen 18 there is no leakage from the tank 24. In this way, if a tank 24 still has e-liquid in the reservoir 28, the tank can be removed and reused, or another user can access the chamber 26 with a different tank 24, without disposing of the tank 24.

Different types of pen configurations can be used in the device 10. In one embodiment of the pen 18 of the device 10, the vaporization chamber 26 is affixed to the battery 22, and therefore, a tank 24 is received by the vaporization chamber plus coil 34 which is already affixed to the battery 22. In another embodiment of the pen 18 of the device 10, the tank includes both the reservoir 28 and the vaporization chamber 26 plus coil 28, and therefore, in such an embodiment the battery 22 threadingly receives the tank 24. In such an embodiment, once the e-liquid is depleted in the tank 24, the reservoir 28 plus vaporization chamber 26 including the coil 34 can be thrown away or at least removed, preferably capped, and set aside for later reuse without any leakage into the battery and other components of the pen 18.

In an embodiment wherein the tank 24 is disposable or can be interchanged or exchanged with another tank 24, remote technology, such as for instance blue tooth technology, on each pen 18 could be provided for programming temperature and time of vaporization for different tanks 24 based on the e-liquid composition, by and through the PCB, which may include memory, and would enable the remote storage of information regarding each tank containing e-liquid preferred vaporization temperature and vaporization time. The feature in this embodiment allows more particular control and/or personalization of a vaping experience whereby a user can retrieve or store information about each e-liquid and therefore mixtures of vaporization products including ideal temperatures of vaporization. It is also contemplated that this information and control be relayed and stored via a universal serial bus ("USB") or micro-USB connection to a computer. Furthermore, a microprocessor could be used to control, maintain, and change temperatures according to different e-liquid profiles in tanks 24.

Moreover, for a non-disposable embodiment whereby the battery can be recharged and the tanks 24 replaced/exchanged, it could be beneficial to monitor the temperature of the coil 32 in order to reach and maintain the temperature of the coil 32 and thus vaporize the desired components of the e-liquid. Therefore, a temperature sensor for reading and recording the temperature of the coil, temperature in the vaporization chamber, the temperature of the vaporization product, and/or the temperature of the e-liquid in the tank 24 could be included in the device 10. Temperature changes and recordings could also be presented in an LED screen located in the body 14 of the device 10.

In addition, a PCB of the pen 18 of the device could be configured to store temperature information and/or to relay the same to a remote storage through blue tooth or remote technology. In this way, the temperature of the coil 32 of the device could be more closely monitored and adjusted for more accurate vaporization.

Whether the device 10 itself is disposable or rechargeable/reuseable, by providing a device 10 whereby tanks 24 containing different e-liquid components in the reservoirs that can be vaporized at the same time but at different temperatures, a customizable vaporization experience is obtainable by the vaporization device 10 according to a user's subjective tastes and experiences, or in the case of medical use, prescribed combinations.

Figure 6:
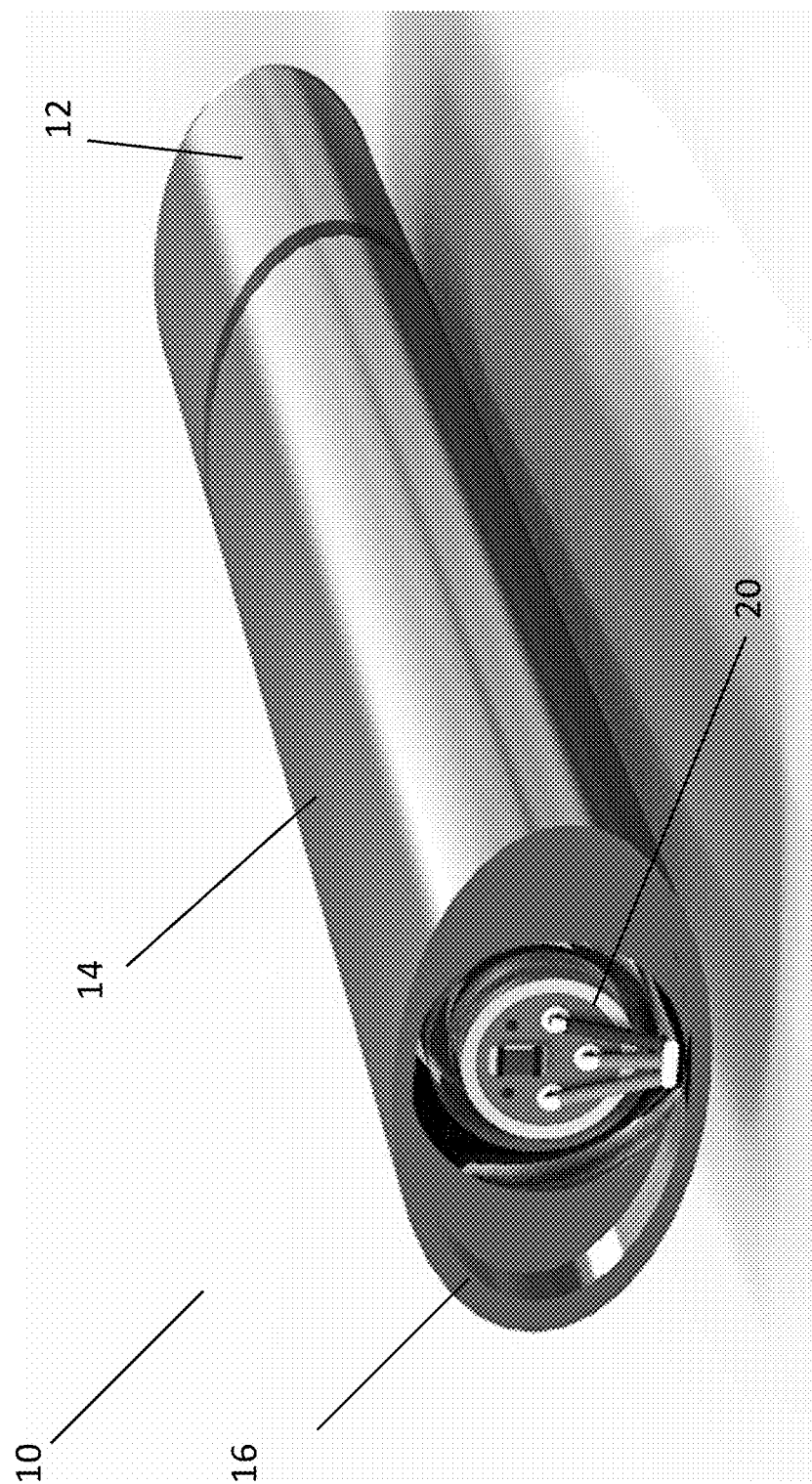
FIG. 6 illustrates an embodiment of the ventilated end of the device in accordance with the principles of the present invention.

In another embodiment, illustrated in FIG. 6, the ventilated end 16 has a single PCB and sensor 20 whereby the plurality of pens 18 housed in the body 14 are controlled by the single PCB and sensor 20, and preferably a microprocessor which can control the temperature of each of the different pens 18 so that an appropriate vaporization temperature can be accommodated by each coil 34 for each tank 24 containing in its reservoir 28 a unique e-liquid. In an embodiment whereby a plurality of pens 18 is controlled by a single PCB and sensor, different tanks 24 which contain an e-liquids of different viscosity than another tank's 24 e-liquid, and which are not combinable in a single tank 24, can still be vaporized at the same time.

Figure 9:
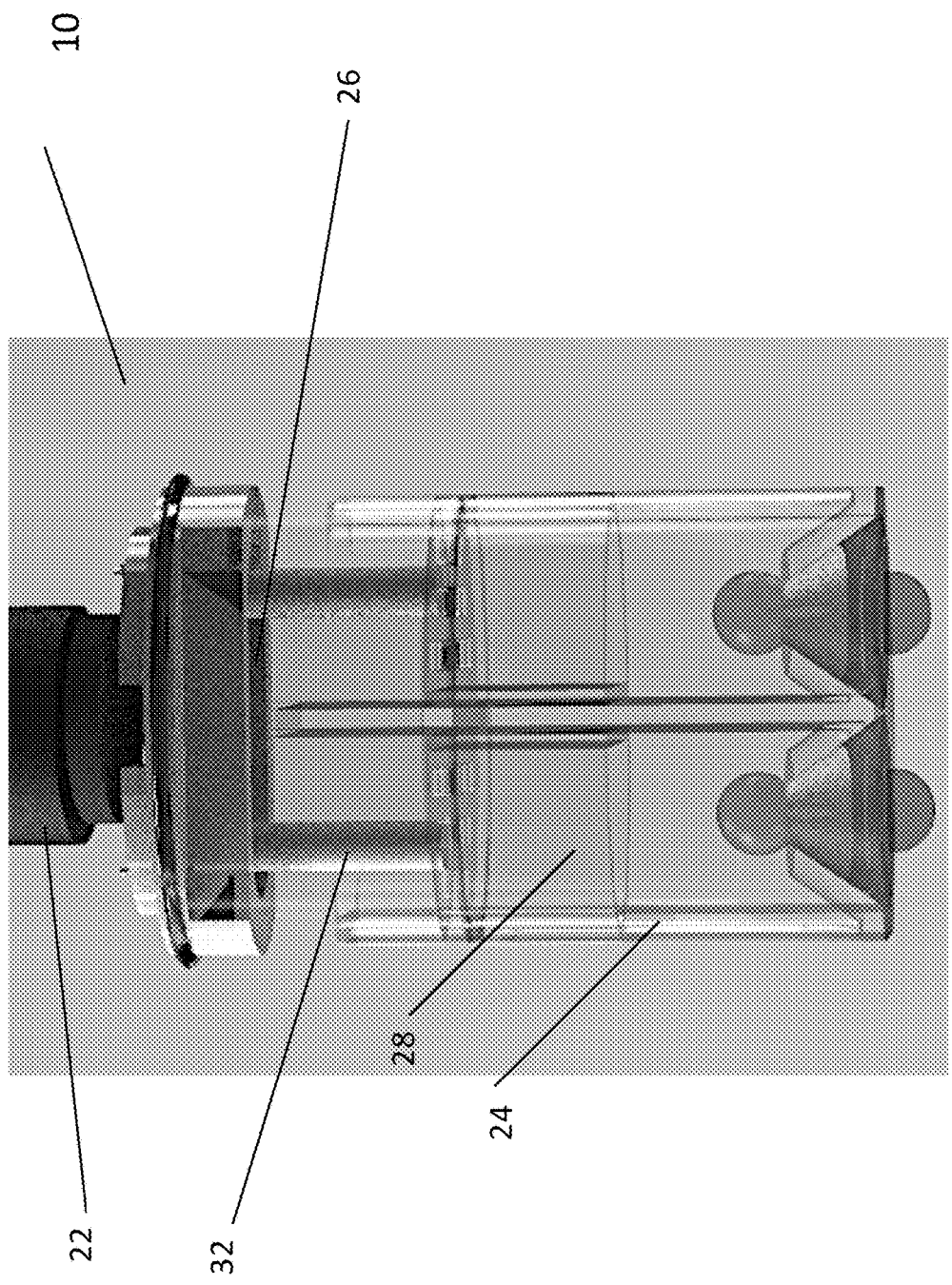
FIG. 9 illustrates an embodiment of a plurality reservoir tank being assembled onto a batter of a pen of the device in accordance with the principles of the present invention.

In yet another embodiment, as in FIG. 9 is illustrated a tank 24 being assembled onto a pen 18, whereby the tank 24 has a plurality of reservoirs 28 each for housing a different e-liquid. Although different e-liquids are provided in the tank 24, they are operationally connected to a single vaporization chamber 26. Though the advantage of mixing during vaporization is present in this embodiment, components of the e-liquid combination in the vaporization chamber 26 are vaporized all together at the same temperature. This embodiment also accommodates e-liquid which is not easily mixed due to the varying percentages of PG, VG, water and components, effecting viscosity. This embodiment also shows a dual wick 32 which allows for the delivery of e-liquid from each of the reservoirs 28 of the tank 24 to be delivered to the vaporization chamber 26 for vaporization at the same time and temperature. The battery 22 is also shown as pertaining to a single pen 18.

Figure 7:
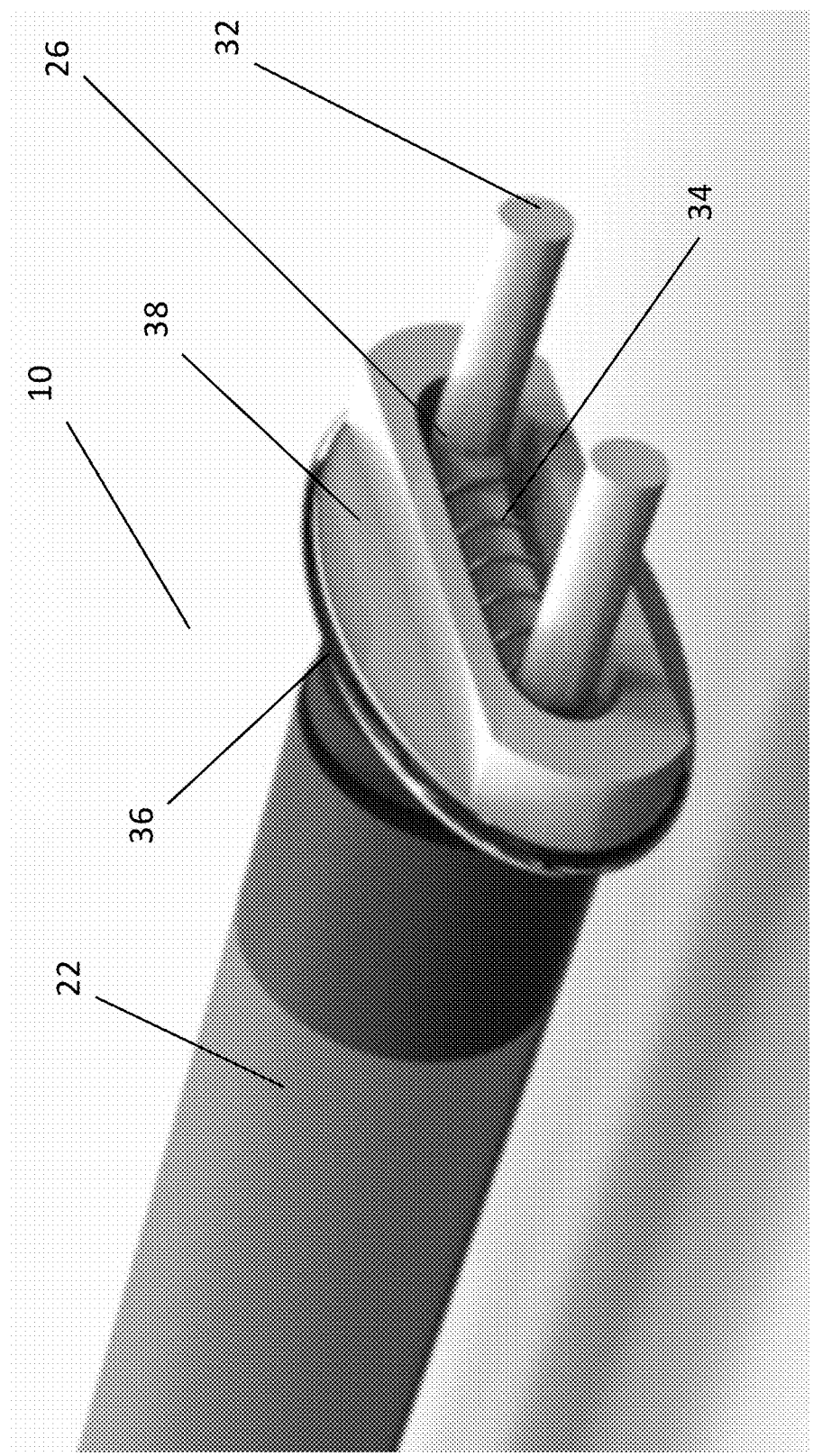
FIG. 7 illustrates an embodiment of the wick, coil and battery of the device in accordance with the principles of the present invention.

FIG. 7 illustrates a coil 34 of the device 10. In this embodiment, the dual wick 32 and coil 34 in the chamber 26 are visible. Also illustrated is a lip or O-ring 36 forming a lip to securely capture a corresponding groove on the plurality reservoir tank 30. In this way, the e-liquid in the tank 24 is less likely to be spilled because the tank 24 is secured on the wick body 38, and any jarring of the device 10 can reduce the chance of e-liquid leaking from the tank 24. In another configuration, the lip 36 can be on the tank 24 while the groove can be formed on the wick body 38. As described above, the coil 34 and vaporization chamber 26 can be contained within a disposable tank 24 whereby the tank 24 is threadingly received by the battery 22, or the coil 34 and the vaporization chamber 26 can be affixed to the battery 22 which is configured to threadingly receive a disposable tank 24 containing the e-liquid.

Figure 8:
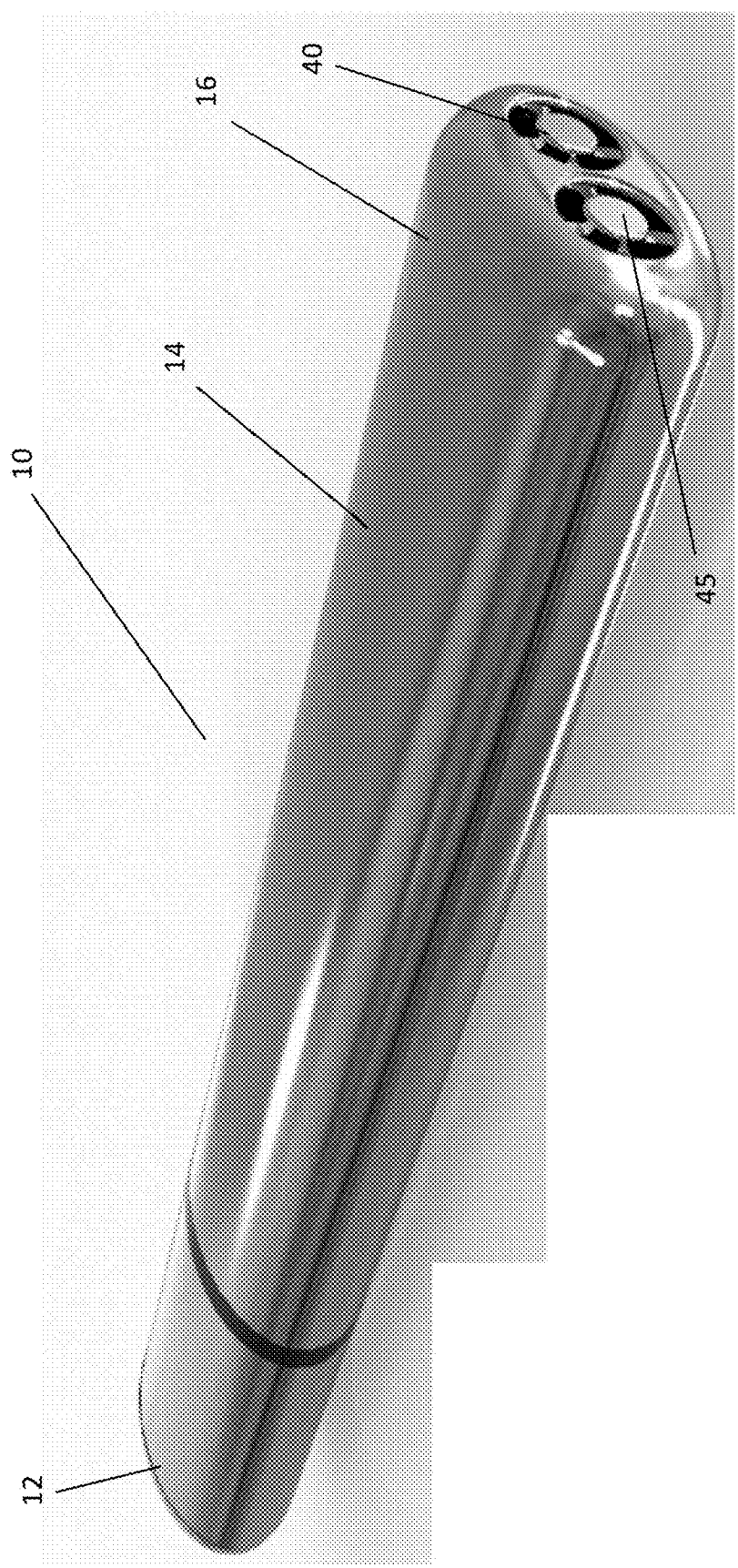
FIG. 8 illustrates an embodiment of the ventilated end showing a vortex tip of the device in accordance with the principles of the present invention.

FIG. 8 illustrates yet another embodiment of the device 10 whereby in the ventilated end 16 there is a vortex tip 40 for better air mixing through the air passage extending from the end 16 through the mouthpiece 12. In this particular embodiment, the body 14 is adjacent to and contiguous with the end 16 and is created as a single piece design. The body 14, and in this embodiment, the end 16, can be made of any material with heat dissipating properties including, for instance, but not limited to, aluminum and stainless steel, and also heat isolating materials that can reduce battery usage, provide heat dissipation properties, while at the same time isolate from the heat inside, such as for instance, but not limited to, plastics, or a combination of materials with heat dissipating and heat isolation properties. Moreover, for embodiments that have rechargeable batteries and disposable tanks, it is also contemplated that for the convenience of the user, a plurality of windows be provided in the body 14 in order to visualize the amount of e-liquid remaining in the plurality of tanks 24.

Figure 10:
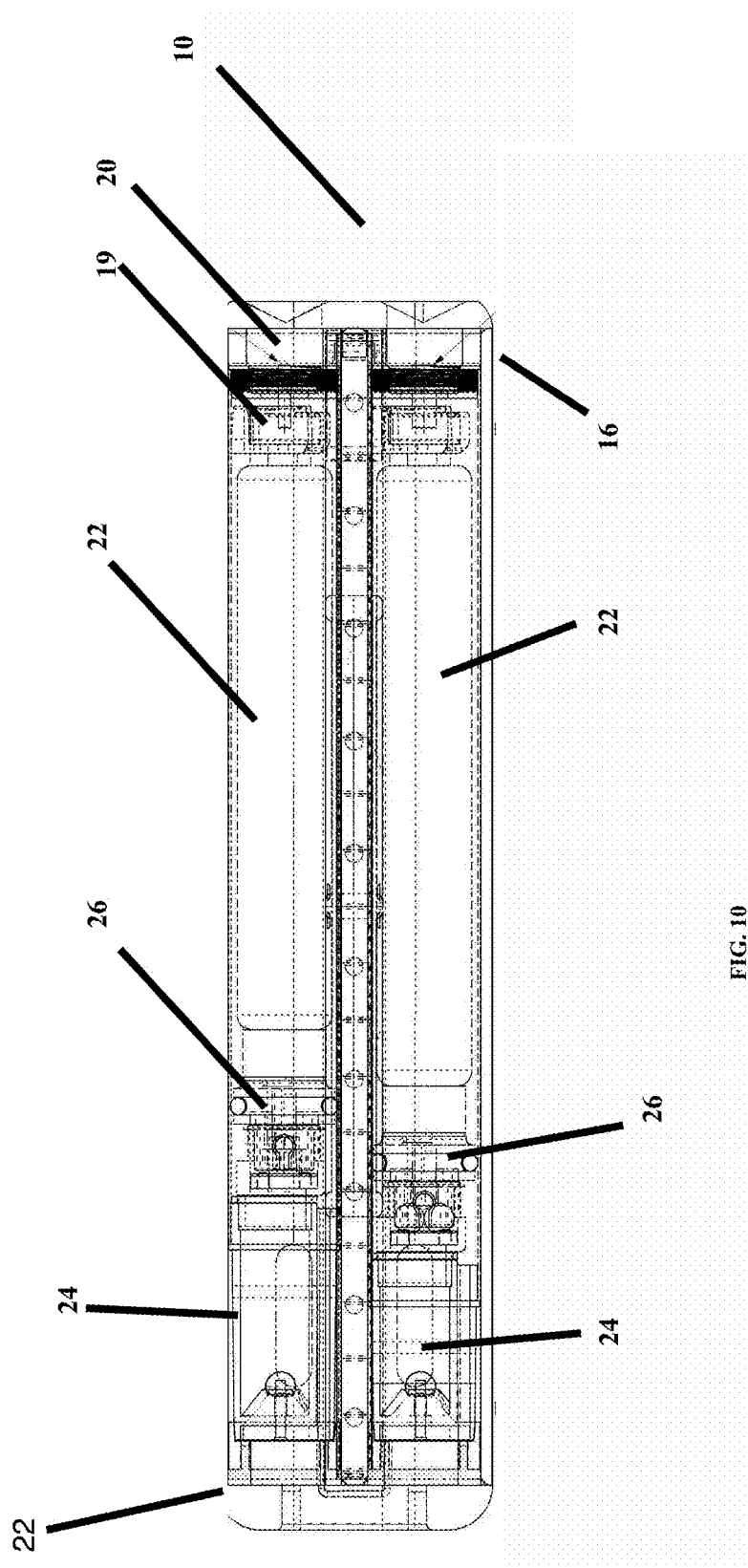
FIG. 10 illustrates a cross-section of an embodiment of the device from the mouthpiece to the ventilated end in accordance with the principles of the present invention.

FIG. 10 illustrates a cross-section of an embodiment of the vaporization device 10 in which there are two batteries 22, one for each of the pens 18, and the batteries 22 are different sizes. As discussed before this is possible and is useful in embodiments where the e-liquid in the different tanks 24 is different and thus may require different voltages and different coils, leading to a need for different sized batteries to most effectively vaporize the e-liquid in both tanks at the same time over multiple vaporization events. In addition, it is optimum to also provide a coil 34 appropriate for vaporization of a particular e-liquid, for example a dual coil could be used for maximum vapor and a single coil for lower temperatures for a different e-liquid. Moreover. FIG. 11 illustrates an embodiment of the vaporization device 10 in an exploded view whereby it can be seen that the mouthpiece 12 is removable from the body 14 and so are the pens 18, potentially to change them or recharge them.

As to the manner of usage and operation of the present invention, the same should be apparent from the above description. Accordingly, no further discussion relating to the manner of usage and operation will be provided.

While embodiments of the device have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A vaporization device comprising:
   a body configured to house at least two pens in a cavity inside the body;
   the at least two pens, each pen comprising a battery, a sensor and a printed circuit board (PCB), wherein the battery is operatively connected to the PCB and a coil, having a first end adjacent and contiguous with a mouthpiece, and a second end adjacent and contiguous with a ventilated end,
   each pen further comprising a plurality of vaporization chambers, each chamber comprising a coil for vaporization and operatively connected to the PCB and battery for controlling the temperature of the coil of each chamber over a vaporization time, wherein each coil can be different from another coil;
   a mouthpiece having an aperture at a first end of the mouthpiece extending into a vapor port which is operatively connected to the plurality of vaporization chambers of the at least two pens at a second mouthpiece end opposing the mouthpiece aperture;
   wherein the body comprises a plurality of airflow apertures for the at least two pens, adjacent to the ventilated end of the at least two pens, and is configured to direct aft flow through the device;
   wherein a plurality of tanks each with a reservoir configured to contain an e-liquid operatively connected to a vaporization chamber; and
   wherein the mouthpiece and tanks are removable, and the batteries are rechargeable.

2. The vaporization device as in claim 1 wherein each chamber of the plurality of vaporization chambers has a tank with a reservoir configured to contain an e-liquid for vaporization, wherein the tank is configured to be received by the pen such that the e-liquid in the reservoir of the tank is delivered to the pen vaporization chamber for vaporization.

3. The vaporization device as in claim 2 wherein the mouthpiece and tanks are removable and the batteries are rechargeable.

4. The vaporization device as in claim 2 wherein the plurality of pens further comprise remote control technology for programming temperature and time of vaporization along with allowing remote storage of information.

5. The vaporization device as in claim 4 wherein each of the pens further comprise a microprocessor.

6. The vaporization device as in claim 1 wherein the plurality of pens further comprise remote technology for programming temperature and time of vaporization along with allowing remote storage of information.

7. The vaporization device as in claim 6 wherein each of the pens further comprise a microprocessor.

8. The vaporization device as in claim 1 wherein the number of airflow apertures is the same as the number of pens in the body.

9. A vaporization device comprising:
   a body configured to house at least two pens, and having a first end and an opposing second end, wherein the second end is adjacent to a ventilated end which comprises a plurality of airflow apertures;
   at least two pens, each having a battery a plurality of vaporization chambers, and a plurality of reservoirs and wherein the battery is operatively connected to a PCB and a sensor;
   a mouthpiece adjacent and contiguous with the first end of the body, wherein the mouthpiece is provided with an aperture at a first end and which extends into a vapor port which is operatively connected to a plurality of vaporization chambers at the end opposing the aperture; and
   a ventilated end adjacent to and contiguous with the second end of the body having a plurality of airflow apertures, wherein the airflow apertures are operatively connected to a sensor;
   a sensor configured to register changes in airflow to the device and to communicate with a PCB;
   a PCB operationally connected to a plurality of coils and each battery of each pen, and configured to control a temperature of each coil in each one of a plurality of vaporization chambers;
   a plurality of vaporization chambers each housing a coil for vaporization operatively connected to the PCB and the battery for controlling the temperature of the coils; and
   a plurality of reservoirs containing e-liquid operatively connected to the coil for vaporization.

10. The vaporization device as in claim 9 wherein the vaporization chambers further comprise a plurality of wicks, and wherein each of the plurality of reservoirs is contiguous with a single vaporization chamber, wherein one of the plurality of wicks is in contact with and is configured to absorb the e-liquid in a reservoir so that e-liquid from each of the reservoirs is delivered by absorption by a wick of the plurality of wicks to the coil, mixed with other e-liquids from other reservoirs from the plurality of reservoirs, in the single vaporization chamber to be vaporized.

11. The vaporization device as in claim 9 wherein each reservoir is contiguous with a single vaporization chamber and coil, independent from other reservoirs, so that e-liquid in the reservoir is delivered to and vaporized from a single vaporization chamber apart from the other e-liquids in the other reservoirs, at the same temperature as e-liquid in the other reservoirs in other chambers, producing a vaporization product delivered to the vapor port for delivery to the user through the mouthpiece.

12. The vaporization device as in claim 9 wherein the mouthpiece is removable and the tanks are removable.

* * * * *